United States Patent
Ringeisen et al.

(10) Patent No.: US 7,381,440 B2
(45) Date of Patent: Jun. 3, 2008

(54) BIOLOGICAL LASER PRINTING FOR TISSUE MICRODISSECTION VIA INDIRECT PHOTON-BIOMATERIAL INTERACTIONS

(75) Inventors: Bradley R. Ringeisen, Alexandria, VA (US); Jason Barron, Alexandria, VA (US); Peter Wu, Ashland, OR (US); David B. Krizman, Gaithersburg, MD (US); Marlene M. Darfler, Derwood, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/863,833

(22) Filed: Jun. 4, 2004

(65) Prior Publication Data
US 2004/0247777 A1    Dec. 9, 2004

Related U.S. Application Data

(60) Provisional application No. 60/542,841, filed on Feb. 10, 2004, provisional application No. 60/476,377, filed on Jun. 6, 2003.

(51) Int. Cl.
*B05D 3/06* (2006.01)
(52) U.S. Cl. .................................. 427/2.11
(58) Field of Classification Search ......... 427/2.1–2.31
See application file for complete search history.

(56) References Cited

U.S. PATENT DOCUMENTS

| | | | |
|---|---|---|---|
| 3,600,319 A | 8/1971 | Gedge et al. | |
| 3,629,723 A * | 12/1971 | Snitzer | 372/19 |
| 4,886,681 A | 12/1989 | Clabes et al. | |
| 4,952,294 A | 8/1990 | Collins et al. | |
| 4,987,006 A | 1/1991 | Willams | |
| 5,156,938 A | 10/1992 | Foley | |
| 5,171,650 A | 12/1992 | Ellis | |
| 5,292,559 A * | 3/1994 | Joyce et al. | 427/597 |
| 5,308,737 A | 5/1994 | Bills | |
| 5,324,591 A | 6/1994 | Georger, Jr. | |
| 5,725,989 A | 3/1998 | Chang et al. | |
| 5,780,971 A | 7/1998 | Dawson et al. | |
| 5,958,268 A | 9/1999 | Engelsberg et al. | |
| 6,008,052 A | 12/1999 | Davis et al. | |
| 6,177,151 B1 * | 1/2001 | Chrisey et al. | 427/596 |
| 6,251,467 B1 * | 6/2001 | Liotta et al. | 427/2.11 |

(Continued)

OTHER PUBLICATIONS

Tolbert et al, "Laser Ablation Transfer Imaging Using Picosecond Optical Pulses: Ultra-High Speed, Lower Threshold and High Resolution", Journal of Imaging Science and Technology, Sep./Oct. 1993, pp. 485-489, vol. 37, No. 5.

(Continued)

*Primary Examiner*—Erma Cameron
(74) *Attorney, Agent, or Firm*—John J. Karasek; Joseph T. Grunkemeyer (57) ABSTRACT

A method of laser forward transfer is disclosed. Photo energy is directed through a photon-transparent support and absorbed by an interlayer coated thereon. The energized interlayer causes the transfer of specific regions of a heterogeneous tissue sample coated thereon across a gap and onto a receiving substrate or into a receiving vessel.

37 Claims, 5 Drawing Sheets

U.S. PATENT DOCUMENTS

| | | |
|---|---|---|
| 6,403,367 B1 | 6/2002 | Cheng et al. |
| 6,541,420 B2 | 4/2003 | Yamamoto et al. |
| 6,805,918 B2 | 10/2004 | Auyeung et al. |
| 6,815,015 B2 | 11/2004 | Young et al. |
| 2002/0015958 A1 | 2/2002 | Audeh et al. |
| 2002/0071901 A1* | 6/2002 | Ringeisen et al. ........... 427/2.1 |
| 2002/0122898 A1 | 9/2002 | Ringeisen |
| 2002/0173033 A1 | 11/2002 | Hammerick et al. |
| 2004/0209316 A1* | 10/2004 | Ritchlin et al. .............. 435/7.2 |
| 2005/0014203 A1* | 1/2005 | Darfler et al. ............... 435/7.2 |
| 2005/0018036 A1 | 1/2005 | Barron et al. |

OTHER PUBLICATIONS

Ringeisen et al., "Generation of mesoscopic patterns of viable *Escherichia coli* by ambient laser transfer" *Biomaterials* 23 (2003) 161-166.

* cited by examiner

Intact Tissue

100 μm

Post Dissection

100 μm

Procured and Disrupted Tissue

BIOLOGICAL LASER PRINTING FOR TISSUE MICRODISSECTION VIA INDIRECT PHOTON-BIOMATERIAL INTERACTIONS

This application claims the benefit of U.S. Provisional Patent Application No. 60/476,377, filed on Jun. 6, 2003 and U.S. Provisional Patent Application No. 60/542,841, filed on Feb. 10, 2004. All applications named are incorporated by reference. U.S. patent application Ser. No. 10/863,850, pending, is also incorporated by reference. This application is the result of a Joint Research Agreement as defined in 35 U.S.C. § 103(c)(3) between the United States Naval Research Laboratory and Expression Pathology, Inc. that was in effect on or before the date the claimed invention was made.

BACKGROUND OF THE INVENTION

1. Field of the Invention

The invention is generally related to methods of laser and/or photon transfer.

2. Description of the Prior Art

Direct write technologies have gained popularity with the increased interest in biological sensors and microarrays, and the push for engineered tissues to replace organ transplants. These techniques allow for increased ability to manipulate biological materials in very small volumes with much better accuracy than has been previously possible. Some of the most promising techniques for use in controlling and transferring biological materials are matrix assisted pulsed laser evaporation direct write (MAPLE DW, see U.S. Pat. No. 6,177,151 to Chrisey et al., incorporated herein by reference), dip-pen nanolithography (DPN), scanning probe microscopy (SPM), microcontact printing (MCP), and laser guidance direct write.

MAPLE DW focuses a pulsed laser source at the interface of a quartz "ribbon" (analogous to a typewriter, it is usually a quartz slide with a coating containing a mixture of a matrix support material and the biological materials of interest) to cause the ablation of a small amount of the interfacial matrix material, which then causes the remaining bulk matrix and biological material to be expelled from the ribbon in a bubble-jetting effect. The expelled material travels through-space, away from the laser and ribbon to a receiving substrate. This results in a spot of transferred material approximately 100 µm in diameter with pL scale volumes. MAPLE DW has limited applications or inherent limitations due to the physical properties of the biological materials and surrounding media needed to ensure accurate pattern formation. Specifically, MAPLE DW requires that a mixture of transfer material and a matrix material be presented to the laser source. The matrix must be of higher volatility than the transfer material and strongly absorb the incident radiation. In addition, the reproducibility of the technique can be low due to inconsistencies in the parameters necessary for ablation of the matrix material. Also, because the absorptivity of certain matrix materials is quite low, there is the potential for damage to biological materials from direct and indirect interaction with the incident laser radiation.

Laser transfer of biological materials presents a challenge due to the fragility of many biological materials. They can be harmed by shear stress when they are removed from the target substrate and by impact stress when they land on the receiving substrate. DNA in particular can be uncoiled by such stresses. Heat can denature many biological materials. UV damage can also result when a UV laser is used.

The analysis of tissue samples, both normal and diseased, benefits greatly from the ability to procure homogenous populations of cells directly from pathologically defined tissue sections where tremendous amounts of cellular heterogeneity can exist. This is the reasoning behind development of tissue microdissection technology as originally developed in the Laser Capture Microdissection (LCM) technology. Tissue microdissection technologies have improved the analysis of tissue samples by providing a means through which molecular profiling of cells derived from tissue samples can be placed in a pathologically relevant context. However, these technologies were originally designed for dissection of frozen tissue samples and not for use on histopathologically processed and fixed tissue samples such as formalin-fixed, paraffin-embedded (FFPE) tissue.

Other tissue microdissection technologies have been patented and tissue microdissection instruments are available on the commercial market including the PixCell systems (Arcturus), the PALM system (PALM Microlaser Technologies), the uCUT (Molecular Machines and Industries), the Leica AS LMD (Leica Microsystems), the LaserScissors (Cell Robotics), the MicroDissector (Eppendorf), and the Clonis system (Bio-Rad).

These techniques generally use one of two methods. One method is a contact method where a thin film is placed on top of and in contact with the tissue so that when a single laser event is used to illuminate through the film from the top, it activates the film to become adherent to the tissue. When the film is subsequently pulled off the tissue, the material is stuck to the underside of the film and the material is then removed from the film by biochemical procurement methods.

Another method utilizes a polyethylene, polyethylene-naphthalene, polyester, polyacrylate, polymer that contains at least 5% by weight of an aromatic or part-aromatic polycondensate coated material situated in between a planar support and the tissue. A primary laser event is used to cut around the cells of interest within the tissue and to separate these cells from the surrounding cells, and then a subsequent second laser illumination event is used to catapult those separated cells upward into a collection vessel. This method constitutes two separate laser illumination events. A third method utilizes a similar polyethylene terephthalate (PET) or polyethylene naphthalate (PEN) coating between the tissue to be dissected and the glass slide as discussed in the previous method, however, this approach relies on laser light to etch a circular boundary around the cells of interest to isolate them from the surrounding tissue after which the process of gravity causes the PET/PEN coating along with the region containing the cells of interest that has been isolated by laser etching to simply fall downwards into a collection vessel.

While each of these systems using these two methods offers unique and useful instrumentation, none were developed and optimized for formalin-fixed/paraffin embedded (FFPE) tissue as the primary tissue source for dissection. Nor have any of these previous approaches involved the transfer of tissue utilizing simple removal of the cells from the tissue by means of a single light illumination event onto a photon-absorbing material to mediate a precisely controlled explosive event for downward expulsion of the cells in a single explosive event from the tissue. The ability to perform tissue dissection from FFPE sections is not efficient with these instruments and the vast majority of tissue dissection practitioners do not utilize these instruments for that purpose. The ability to dissect cells directly from FFPE tissue sections would be advantageous.

SUMMARY OF THE INVENTION

The invention comprises a method for microdissecting tissue materials comprising the steps of: providing a receiving substrate or collection vessel, providing a target substrate, providing a source of photon energy, and directing the photon energy. The target substrate comprises a photon-transparent support, a photon-absorbent interlayer coated on the support, and a transfer material comprising a histopathologically processed or frozen tissue/cell materials coated on top of the interlayer opposite to the support. The photon energy is directed through the transparent support so that it strikes the interlayer. A portion of the interlayer is energized by absorption of the photon energy, which causes a transfer of a portion of the tissue/cell material across a gap between the target substrate and the receiving substrate and onto the receiving substrate or into the collection vessel.

DETAILED DESCRIPTION OF THE EXAMPLE EMBODIMENTS

The primary use of this invention is the isolation, removal, and procurement of specific and defined populations of cells directly from complex histopathologically processed tissue/cells from any organism, as for example the removal of diseased cells from a mixture of diseased and normal cells within a complex tissue derived from formalin fixed mammalian tissue. Once isolated the cells can be used to procure specified biomolecules where each type of biomolecule can be assayed so that the results of such biochemical assays can be correlated directly to the type of cell that was procured by this invention. Therefore the primary implication of this invention is to provide an advanced method to aid in directly correlating changes in biomolecules with diseased cells and the disease processes in which those changes are involved.

The present invention relates to a tissue microdissection process that utilizes a conductive or semi-conductive, photon-absorbing, interfacial coating layer to mediate light-based microdissection, excision, and procurement of cells, groups of cells, and sub-cellular regions of cells directly from histopathologically processed biological samples, histopathologically processed tissues, histopathologically processed cells, frozen tissue or frozen cells.

The invention can provide an efficient, rapid, user-friendly option for the separation, isolation, removal, microdissection, and collection of groups of cells, individual cells, and subcellular regions of cells from histopathologically processed cells and tissue, such as formalin fixed paraffin embedded cells and tissue, that is amenable to computer-aided design/computer aided manufacturing (CAD/CAM) automation. This method can use a non-contact, single light-event for the simultaneous separation, microdissection, removal, and procurement of cells, groups of cells, and sub-cellular regions of cells directly from histopathologically processed biological samples, histopathologically processed tissues, and histopathologically processed cells.

There are currently two standard methods employed to perform microdissection of cells from tissue. The present method differs from these two methods in that it is a non-contact method that use no photo-activating film for adherence to the tissue, and where the separation of cells from the surrounding cells/tissue and transfer of those cells into a collecting device occurs simultaneously as a result of a single light illumination event mediated by a photon-absorbing interfacial layer to cause explosion of cells directly from the tissue. The invention can provide a method for transfer of tissue that allows for control of material placement and volume, and prevents damage to biological structure and function.

An aspect of the present invention uses a light-based, photon-absorptive transfer methodology that specifically relies on a conductive or semi-conductive photon-absorbing transfer layer in order to mediate energy transfer when the energy of the light is high enough (range of 0.1 mJ/cm$^2$-10,000 mJ/cm$^2$) and specific enough to interact with the transfer coating. This interaction is intended to be of sufficient energy to cause transfer due to one or more of the following three potential mechanisms; 1) an ablative explosive mechanism, 2) a photo-thermal mechanism, and/or 3) a photo-mechanical mechanism. The result of this interaction when impacted by the light results in partial and/or total disruption of the tissue. Particular examples of the histopathologically processed biological samples are frozen or chemically-fixed (chemicals including but not limited to formalin and ethyl alcohol) tissue/cells, formalin-fixed paraffin embedded (FFPE) tissues/cells and FFPE tissue blocks, and tissue culture cells that have been chemically fixed by chemicals that include but not limited to formalin and ethyl alcohol, and paraffin embedded.

The invention uses photon energy, such as a laser, incident upon an interlayer to induce tissue or cellular material to be forward-transferred through space to a receiving substrate, microns to millimeters away from the target support. This eliminates the requirement of a laser-matrix interaction as in MAPLE DW. The interlayer converts photon energy into thermal energy. Laser absorption and energy conversion by the interlayer results in the transfer of the tissue or cellular material though one of a number of mechanisms. Tissue microdissection may be done at ambient temperatures conditions. The technique allows for transfer of very small transferred areas (micrometer scale).

The method can have several key advantages over MAPLE DW. Laser interaction with the transfer layer is indirect. This means that virtually any tissue material in a wet or dry condition can be microdissected without having to consider its ability to absorb incoming radiation, which is an imperative requirement for a successful MAPLE DW transfer. This also means that laser absorption can be essentially constant across materials and therefore, accurate transfers can be easier and reproducibility can be greatly increased. Further, interaction of the laser with the transferred tissue material is substantially eliminated. This reduces the possibility of genetic or biological damage from the relatively high energies of the focused laser beam. As the biological layer also acts as the laser absorption layer in MAPLE DW, transfer conditions can vary greatly due to changes in the biological layer, altering the laser adsorption properties that are central to achieving the successful transfer of material. Calculations show that much of the laser energy (>99%) passes completely through the liquid, raising the possibility that the UV laser light could damage the biological material (Parkinson et al., "Absorption cross-section measurements of water vapor in the wavelength region 181-199 nm," *Chem. Phys.*, 204(31), 31 (2003)). Single and double strand comet assays have shown little to no observable genetic damage to the cells, but UV exposure could still hinder other aspects of biological activity via radical formation and cellular response to the UV. Finally, controlling the MAPLE DW transfer process for biological materials is more difficult, due to their poor UV absorption properties (aqueous mediums). In essence, the laser is absorbed by and could cause vaporization through the entire volume of material with which it interacts. This can lead to problems in attaining reproducible results.

The technique allows for the stepwise microdissection of tissue materials without the use of masks or patterning techniques. Because of the transfer mechanism, it is possible to microdissect virtually any tissue, independent of physical properties such as phase, viscosity, homogeneity, and light absorbance. This method also can allow for rapidly transferring a large number of cells of the same type or a variety of types in any order and in close proximity. With no direct contact with the receiving substrate, there is less concern about contamination and with the relatively small transfer volumes, it is possible to obtain very accurate transfer placement.

Figure 1:
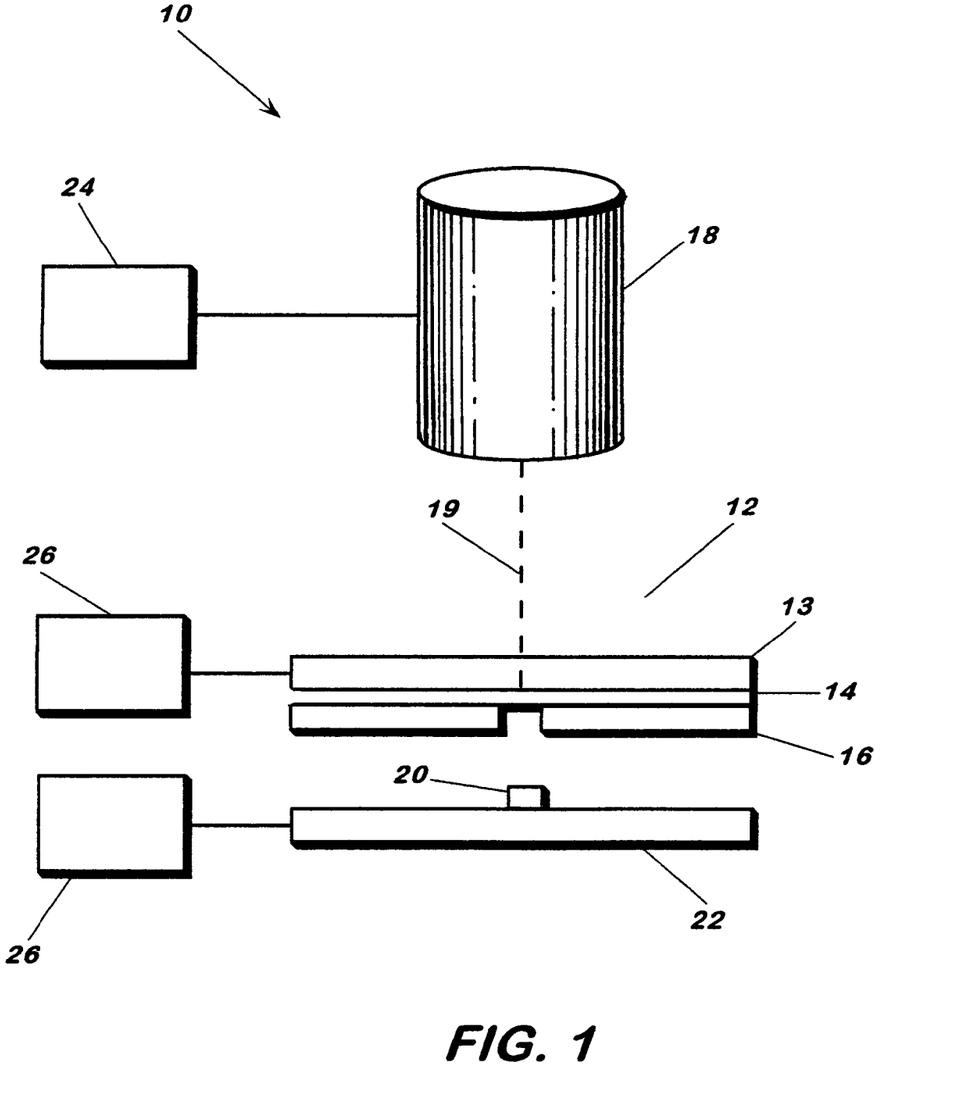
FIG. 1 schematically illustrates an apparatus used to perform the method of the invention.

FIG. 1 schematically illustrates an apparatus 10 that may be used to perform the method of the invention. The apparatus 10 includes a target substrate 12, which comprises a photon-transparent support 13 having an interlayer 14 coated thereon, and a transfer material 16 coated on the interlayer. The transfer material comprises the tissue material. A pulsed laser 18 sends laser pulses 19 into the target substrate and through the support. The pulses are absorbed by the interlayer, which causes a portion 20 of the transfer material to be transferred to a receiving substrate 22. The target substrate, the receiving substrate, and the photon energy source can be moveable with respect to each other.

Control of the beam can be done via an optical stage 24 and manipulation of the target and receiving substrates can be accomplished by computer-controlled stages 26 and CAD/CAM programs that allow for design of complex shapes, and patterns and the microdissection of different tissue materials in a precise and ordered manner. Independent manipulation of ribbon and substrate can be done via a computer-controlled stage.

The source of photon energy may be any photon source that provides sufficient photons to cause the transfer. A suitable photon source is a laser, such as a continuous laser or a pulsed laser. The fluence of a pulsed laser should be chosen such that the transfer is accomplished without causing any undesirable damage to the tissue material, with or without removal of the interlayer. Pulsed lasers are commercially available within the full spectral range from UV to IR. Typically, such lasers emit light having a wavelength in the range of about 157-10600 nm, a pulsewidth of about $10^{-12}$-$10^{-6}$ second and a pulse repetition frequency of about 0 to greater than 100,000 Hz. Examples of suitable lasers include, but are not limited to, excimer lasers operating at 193 and 248 nm and frequency quadrupled or tripled Nd:YAG laser operating at 266 and 355 nm. Suitable ranges of fluence include, but are not limited to, from about 1 to about 1000 mJ/cm$^2$, at least about 0.1 mL/cm$^2$, and at least about 1 nJ/cm$^2$. A 193 nm Lambda Physik 300 ArF excimer laser or a frequency tripled Nd:YAG laser (355 nm) may be used for transfers. The dimensions of the laser energy can be controlled by any means known in the art so that only a precisely defined area of the target substrate is exposed to the laser energy and so that only a precisely defined portion of the transfer material is exposed. The laser energy can be focused through an objective or lens to narrow the beam and expose a smaller portion of transfer material. The beam can be focused down to an approximately 10-150 μm spot size at the ribbon interlayer. This increases the possible resolution of the microdissected and transferred tissue material. Other suitable photon sources include, but are not limited to, a flash lamp and a maser. A flash lamp may be more divergent and require optics to force the light to propagate parallel/co-linear.

The photon-transparent support can be made of any material that is substantially transparent to the particular photons that make up the photon energy. Suitable support materials include, but are not limited to, quartz, a glass, a salt, and a polymer. Quartz is suitable when UV photons are used.

The interlayer can be made of any material that significantly absorbs the photon energy, and may be inorganic. Suitable interlayer materials include, but are not limited to, a metal, a metal oxide, titanium metal, titanium dioxide, chrome, molybdenum, gold, and a polymer, and may comprise more than one layer. Suitable ranges of thickness of the interlayer include, but are not limited to, 10 Å to 10 μm and 5 to 100 nm.

Tissue sections may be placed on the target substrate whole. The surface of the target substrate can be broken into separate regions with different tissues in order to be able to deposit different tissue materials without having to change the target substrate.

The tissue material can be any tissue. In some embodiments, the transfer material also comprises a biomatrix along with the tissue material. The biomatrix can be any material that is compatible with the tissue material and that does not prevent the transfer. The biomatrix may contribute to sustaining the biological activity and/or integrity of the biological and tissue material. Suitable biomatrices include, but are not limited to, water, glycerol, phosphate buffered saline, Tris buffer, and mixtures thereof.

Figure 2:
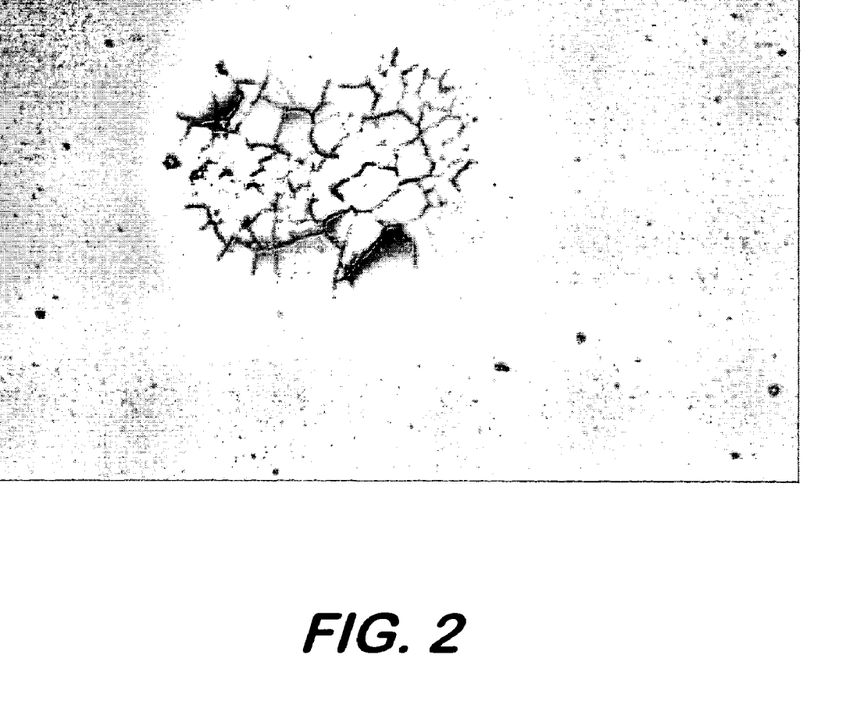
FIG. 2 shows a micrograph of an interlayer that was not removed by a laser pulse.

In some embodiments, the interlayer will remain substantially intact and adhered to the substrate when it absorbs the laser energy. A micrograph illustrating this effect is shown in FIG. 2. The titanium interlayer remained intact, although with mild damage due to rapid heating and cooling. In this case, the mechanism of transfer may be, but is not limited to, photomechanical and/or photothermal shock. This effect may be useful when the tissue material to be transferred may be damaged by exposure to higher levels of energy. The laser penetration into the interlayer may be significantly less than the overall layer thickness. Models show that the temperature gain in the interlayer may be about 100-1000 K, but that less than 5% of the transfer material reaches temperatures greater than ambient.

A portion of the biomatrix adjacent to the energized interlayer may be evaporated to cause the transfer. In this case the laser energy is absorbed by the interlayer and rapidly converted into thermal energy. The superheated interlayer then causes flash ablation of a thin, interfacial portion of the biological support layer, which in turn forces jettison of the bulk tissue materials. The transfer layer consists of a mixture of the biomaterial and supporting biomatrix.

Figure 3:
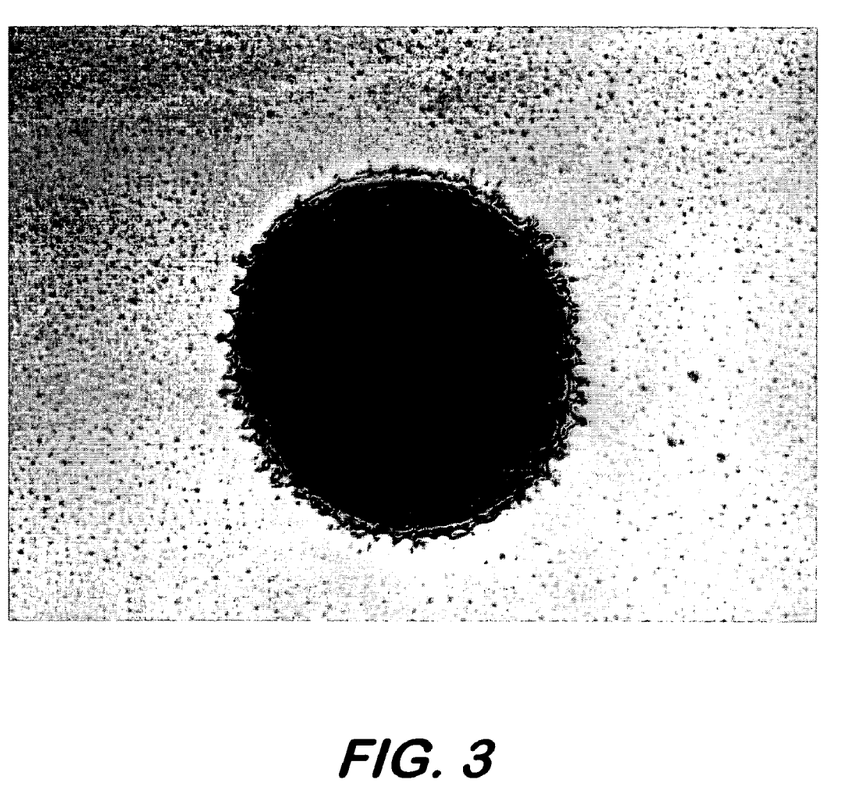
FIG. 3 shows a micrograph of an interlayer that was ablated by a laser pulse.

In some other embodiments, the interlayer may be removed or ablated from the target substrate when it absorbs the photon energy. A micrograph illustrating this effect is shown in FIG. 3. Evidence of explosive removal of the titanium layer can be seen around the edges of the laser-interlayer interaction region. However, this mechanism may be useful when larger portions of a tissue, such as certain entire cells, are transferred. Some cells may be robust enough to withstand such higher levels of energy from the ablated interlayer or from direct exposure to the photon energy. Either mechanism may be appropriate when cells are transferred, depending on the type of cell.

The process can be repeated, exposing additional spots on the target substrate, so that multiple deposits of biological and tissue material can be transferred to the receiving substrate. The receiving substrate can also be a receptacle for collecting the transferred material.

Models suggest that the laser absorption layer acts as an energy conversion material, converting the radiant laser energy via absorption and conduction into heat, which then flows through the remaining absorption layer to the interface with the tissue layer. Calculations of laser penetration into the laser absorption material show that it is significantly less than the total layer thickness, thereby eliminating potential damage by incident UV radiation. Transient heat conduction models show temperature gains in the laser absorption layer of 1400 K under typical laser and material conditions. The effects of thermal stress upon the solid materials, their spatial displacements and the formation of thermal shock waves are under investigation.

When using nanosecond laser pulses, thermal forces may drive the printing mechanism. The ejection of transfer material away from the target may occur as a result of heat transfer through the absorption interlayer and subsequent vaporization of a portion of the transfer material in direct contact with the heated layer. Alternatively, by utilizing near-ultrafast laser pulses, laser forward transfer experiments may be driven by mechanical forces, namely shock waves.

To measure the risk of UV exposure to the biomaterial during the printing process, the percentage of UV laser energy that is absorbed in the metal and metal oxide interlayer film was calculated. Biomaterial transfer is achieved by focusing the laser at the interface of the laser absorption layer and the optically transparent support layer. The exponential absorption coefficient is based upon the calculated penetration depth (skin depth) for the metal. The calculated skin depths at 266 nm for the two metals used as targets are given in Table 1.

TABLE 1

| Interlayer material | Interlayer thickness | Conductivity ($\sigma$) ($\Omega^{-1}$ $m^{-1}$) | Skin Depth ($\delta$) (nm) |
| --- | --- | --- | --- |
| Au | 35 nm | 4.5e7 | 2.2 |
| Ti | 75 nm | 2.4e6 | 9.7 |
| $TiO_2$ | 85 nm | — | 10.5[1] |

[1]"Skin Depth" for $TiO_2$ calculated from $\delta = 1/\alpha$, $\alpha = 4 \cdot \pi \cdot k/\lambda$, k = 2 (average of k⊥ and k∥)

The metal layer thickness used on the targets is much greater than the skin depths. Thus, greater than 99.9% of the non-reflected incident laser energy is absorbed by the solid metal prior to arriving at the absorption layer-biomaterial interface. The $TiO_2$ layer also absorbs the radiation at 266 nm as indicated by the estimated "skin depth" ($\delta=1/\alpha$) calculated from the complex index of refraction (n+ik) and the absorption coefficient ($\alpha \equiv (4 \cdot \pi \cdot k)/\lambda$). Using this calculation, it is estimated that greater than 99.9% of the incident laser energy is also absorbed by the $TiO_2$ absorption layer prior to any interaction with the biomaterial.

In order to understand the role of heat transfer during the process, the energy transfer from the laser to the laser absorption layer was modeled by the time-dependent heat-transfer equation (parabolic formulation) with a source function given by the Lambert-Beer Law. The composite material heat-conduction equation was solved with a finite-element software package (FlexPDE). The models suggest that the laser absorption layer acts as an energy conversion material, converting the radiant laser energy via absorption and conduction into heat, which then flows through the remaining absorption layer to the interface with the biolayer. The process may be a completely interfacial phenomenon. Calculations of laser penetration into the laser absorption material show that it can be significantly less than the total layer thickness. Transient heat conduction models of laser irradiation of the laser absorption layer show temperature gains in the laser absorption layer from 150 to 450 K, increasing with laser fluence. Heat transfer through the laser absorption layer shows little dependence on absorption material thickness, as long as the thickness of the absorption layer was greater than the penetration depth (skin depth) of the laser. The effects of thermal stress upon the solid materials, their spatial displacements and the formation of thermal shock waves are under investigation.

In contrast to the rapid energy conversion and transfer seen in the laser absorption layer, thermal penetration into the much thicker aqueous biomaterial layer (10 to 100 μm thick) is observed to be negligible. Experimental results demonstrate that at 50 ns post-irradiation thermal penetration is calculated to be less than 400 nm into the biolayer. Even 500 ns post-irradiation, the penetration is only 1.2 μm into the biolayer. Further, this model is an upper limit for thermal penetration, as it uses an insulation model that does not allow for thermal cooling. In addition, the model does not account for the vaporization of the material that would occur as soon as the biomaterial at the interface reaches 400 K. Vaporization at the interface will reduce the amount of thermal penetration by acting as an insulation layer and by reducing the ambient heat via heat of vaporization. While the current model predicts that the first 5% of the material nearest the interlayer is affected, it is likely that the amount of material actually affected is much less.

The invention can be used with tissue samples modified according to a dehydration/rehydration process. More specifically, the samples of the present invention may be histopathologically processed tissues. These samples may be treated using biochemical methodology, allowing subsequent dissection and removal of individual cells, groups of cells, and/or parts (sub-cellular regions) of individual cells directly from the modified tissue sample.

Figure 4:
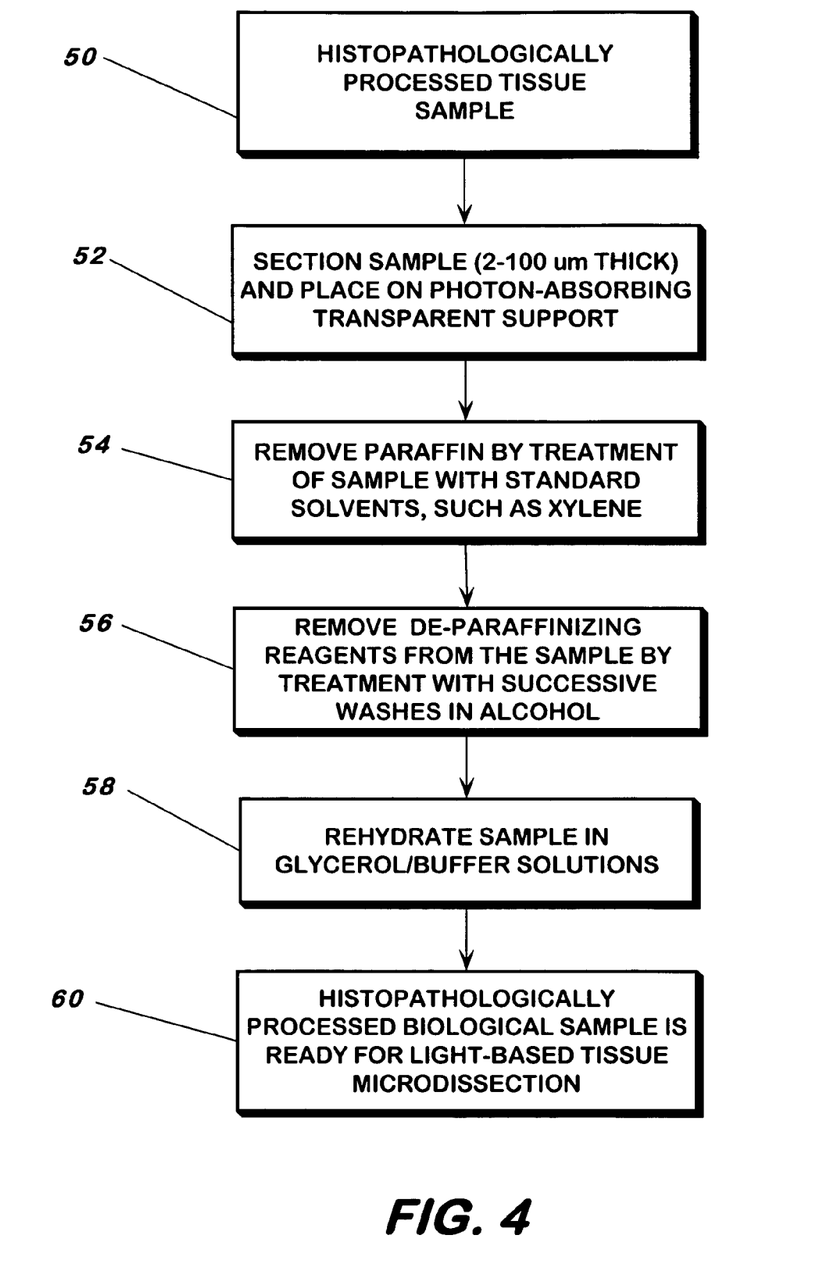
FIG. 4 shows a flow chart of a method of preparing a tissue sample for laser transfer.

An embodiment of the present invention is illustrated in the flow chart of FIG. 4. This embodiment relates to a method comprising the following steps.

(a) Identification 50 of histologically processed and/or archived biological samples, histopathologically processed tissues, or histopathologically processed cells from sources including biological samples from research experiments, biological samples from clinical laboratories such as cytological smears and preparations, biological samples from tissue archives, blood drawn from organisms, biopsies from clinical laboratories or hospitals, and any tissue/blood sample from any organism that has been histopathologically processed. Histopathologically processed biological samples is defined as tissues or cells obtained from any biological source from any organism that may have been treated with chemical staining reagents, including but not limited to hematoxilin and eosin, and chemical fixative agents, including but not limited to formalin and ethyl alcohol, in order to visualize and maintain the tissue/cellular structure and preserve the biomolecules within the sample. Freshly frozen tissue and cells are also within the embodiment of this definition of a histopathologically processed biological sample. The use of embedding compounds, including but not limited to wax and paraffin, can be and usually is part of the histopathologic processing but is not necessary within the scope of this invention.

(b) Perform sectioning 52 of histopathologically processed sample as in (a) within a range from about 1 μm to 60 μm in diameter. The sectioning can be performed by standard sectioning methods, such as that which is achieved with a microtome.

(c) Placing 52 thinly sectioned material as described above in (a) onto a photon transparent support such as plastic, glass, or quartz that has previously been coated with a thin layer in a range from about 1 angstrom to 10 μm thick of conductive or semi-conductive photon-absorbing material, such as chrome, gold, or titanium or like materials and/or their derivatives.

(d) Deparaffinize 54 the tissue section by means of standard treatment with de-paraffinizing reagents, including but not limited to xylenes and/or SubEx, which is standard procedure for histopathological processing of tissue.

(e) Removal 56 of the de-paraffinizing reagents from the sectioned sample by treatment with successive washes in alcohol (for example ethyl alcohol (f) Re-hydrating 58 with a mixture of glycerol and buffer where the glycerol ranges from 20% to 60% glycerol in a specific buffer type and pH. Both buffer type and specific pH requirements are known to those well versed the arts.

(g) Performing one of any number of standard tissue/cell staining procedures in order to aid identification of cells for microdissection of specific cells, groups of cells, and/or subcellular regions of cells.

In the method of this part of the present invention, histopathologically processed biological samples, histopathologically processed tissues, and histopathologically processed cells are prepared specifically for microdissection of cells, groups of cells, individual cells, and subcellular regions of cells utilizing the novel microdissection methodology described in detail below. Particular examples of histopathologically processed biological samples are formalin-fixed tissue/cells, formalin-fixed/paraffin embedded (FFPE) tissues/cells and FFPE tissue blocks, and tissue culture cells that have been formalin-fixed and formalin-fixed/paraffin embedded.

The transfer method may be performed specifically according to the following steps:

(a) Placing a tissue sample onto a photon transparent support such as plastic, glass, or quartz that has previously been coated with a thin layer in a range from about 1 angstrom to 10 μm thick of conductive or semi-conductive photon-absorbing material, such as chrome, gold, or titanium or other like materials and/or their derivatives.

(b) Preparing sample according to the de-paraffinizing/dehydration/rehydration protocol of tissue samples as described above and diagrammed in FIG. 4.

(c) Utilizing the microscopic properties of this process, encompassing a microscope objective that ranges from 1× to 100× in magnification, a video camera, and a video screen for viewing, to visually identify cells, groups of cells, and/or subcellular regions of cells by the staining procedure as described above to determine which cells, groups of cells, and/or subcellular regions of cells to microdissect and procure from the prepared tissue sample that resides on the photon transparent support with the thin layer of conductive or semi-conductive photon absorption material.

(d) Directing a source of light, for example a white light or a laser, through a standard or non-standard microscope objective, ranging from 1× to 100× magnification and that has been positioned directly above the biological sample in order to directly focus the light to a fine, precise, and directed beam that ranges from 0.05 um to 200 um in diameter for directly illuminating on the cells, groups of cells, and/or subcellular regions of cells identified for microdissection and procurement.

(e) Illuminating the above-described highly focused beam of light (for example white light or laser light) onto the region of photon-absorbing material, in a single light illuminating event, under which the tissue containing the cells, groups of cells, and/or subcellular regions of cells identified and chosen for microdissection, excision, and procurement exist in order to ablate, or not ablate and simply heat, a portion of the previously described thin layer of conductive or semi-conductive photon-absorbing material (such as chrome, gold, or titanium or other like materials and their derivatives) causing explosive activity mediated by a either an ablative/explosive mechanism, a photo-thermal mechanism, and/or a photo-mechanical mechanism within the photon-absorbing layer resulting in precise and directed physical disruption of the tissue to separate, remove, explode and/or transfer cells, groups of cells, and/or subcellular regions of cells identified for microdissection and procurement from the tissue.

(f) Collecting and procuring the cells, groups of cells, and/or subcellular regions of cells that have been physically separated, removed, exploded, and/or transferred from the tissue residing on the photon transparent support and the photon-absorbing material by the single, focused beam of light into a receiving receptacle, as for example a microcentrifuge tube or multi-well plate.

(g) Collecting any number of these multiple regions in the same receiving receptacle or in different receiving receptacles resulting from any number of individual and single light focusing and illuminating events that lead to physically removing, exploding, and/or transferring multiple and different regions of cells, groups of cells, and/or subcellular regions of cells from the tissue residing on the photon transparent support and the photon-absorbing interfacial layer by the focused beam of light.

(h) Utilizing the cells, groups of cells, and/or subcellular regions of cells that have been physically separated, removed, exploded, and/or transferred from the tissue residing on the photon transparent support and the photon-absorbing interfacial layer by the focused beam of light into a receiving receptacle in any type of physical assay, biochemical assay, visual assay, biological assay, proteomic assay, genomic assay, or general molecular biology assay in either a research, research and development, or clinical setting.

An aspect of the method of the present invention of performing light-based photon absorption-mediated microdissection of histopathologically processed biological samples, tissues, and cells, includes the processing of the histopathologically processed biological sample and the photon-absorbing interfacial layer that mediates precise and controllable impact of energy from a light-based source to an explosive mechanism in order to impart directed removal of specific cells, groups of cells, and/or subcellular regions of cells from biological samples that were previously processed by histopathological methods. An example of such a biological sample previously processed by histopathological methods is formalin-fixed paraffin embedded mammalian tissue/cells.

Figure 5:
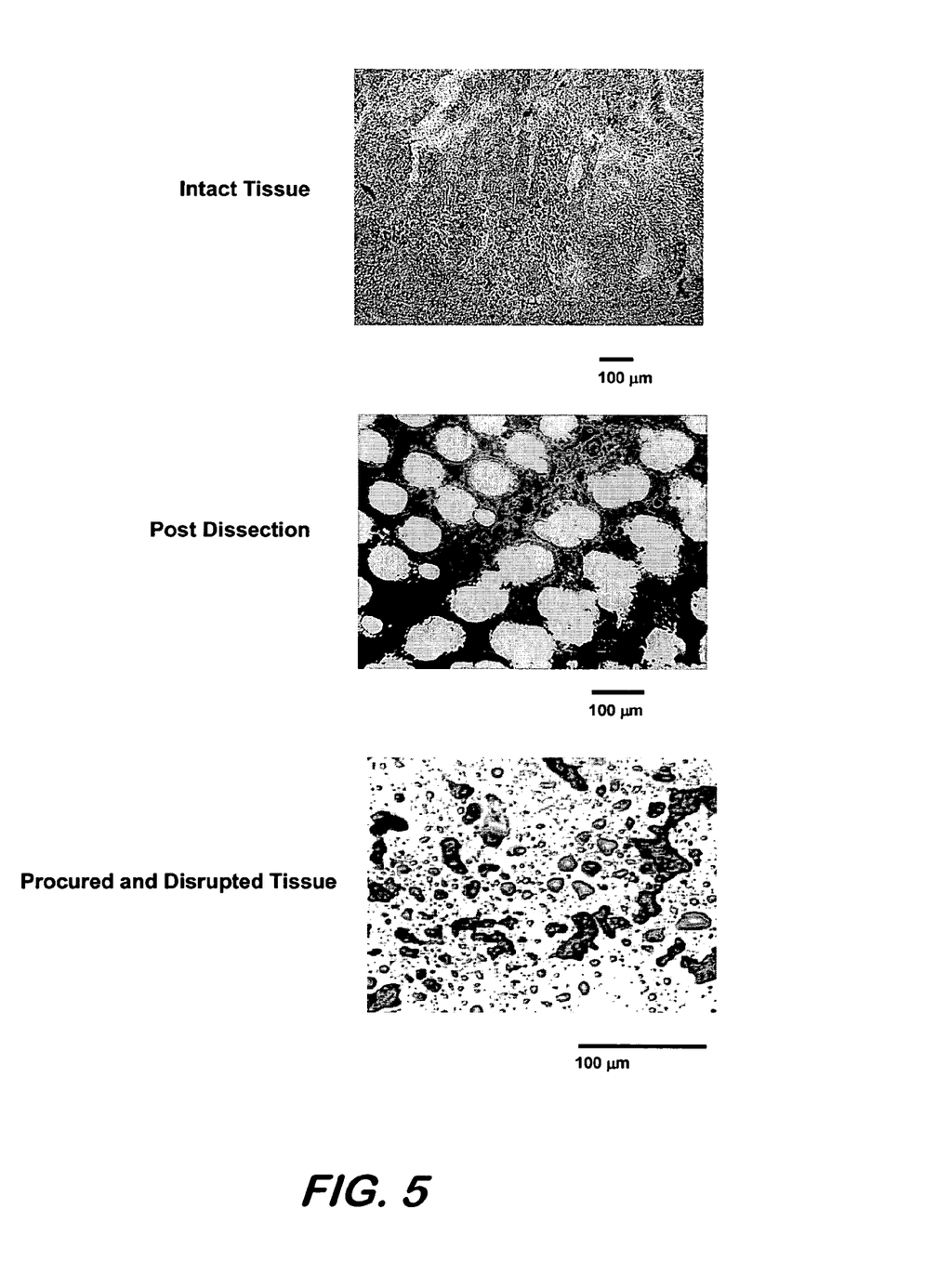
FIG. 5 shows results when this method is applied to histopathologically fixed and processed tissue.

An example demonstrating the results of such a tissue microdissection process as described is shown in FIG. 5. The left panel is the fixed tissue sample before laser illumination. The middle panel shows this tissue after laser transfer where the circles are the holes that are left behind after the laser illuminates through the tissue and the photon-absorbing interfacial layer. The holes are measured at 80 um in diameter, the exact diameter of the laser beam used for the transfer illuminating events. The right-most panel shows the disrupted tissue resulting from a single laser illuminating and transfer event, where the tissue was deposited on a glass slide for viewing under a microscope.

This method encompasses the concept of tissue microdissection as practiced in numerous ways for the excision of cells from thin sections of biological samples. The present method is unique in that it excises specific cells, groups of cells, and/or subcellular regions of cells directly from uniquely processed FFPE tissue utilizing a unique processing method for the biological sample and a forward transfer mechanism based on the transition from light energy (ex. white light or laser) into an explosive energy mechanism mediated by a thin photon-absorbing layer that is in precise contact with the histopathologically processed biological sample to propel the specific cells, groups of cells, and/or subcellular regions out of its previous tissue structured environment into a collecting tube or vessel.

Applications of this technology include specific and precise removal and procurement of homogeneous populations of cells from a complex mixture of cells that reside within a cellularly heterogeneous and complex histopathologically processed biological sample and tissue material. Applications of this technology also include specific and precise removal and procurement of subcellular regions, areas, and organelles of cells within complex histopathologically processed biological samples and tissue material.

Obviously, many modifications and variations of the present invention are possible in light of the above teachings. It is therefore to be understood that the claimed invention may be practiced otherwise than as specifically described.

We claim:

1. A method for microdissecting histopathologically processed tissue/cell materials comprising the steps of:
   providing a receiving substrate or collection vessel;
   providing a target substrate comprising a photon-transparent support, a photon absorbent interlayer coated on the support, and a transfer material comprising histopathologically processed or frozen tissue/cell materials characterized by cellular heterogeneity coated on top of the interlayer opposite to the support;
   wherein the interlayer comprises a metal oxide;
   providing a source of photon energy;
   selecting particular cells, groups of cells, or sub-cellular regions to be microdissected from the tissue by the photon energy; and
   directing the photon energy through the transparent support so that it strikes the interlayer;
   wherein a portion of the interlayer is energized by absorption of the photon energy; and
   wherein the energized interlayer causes a transfer of the particular cells, groups of cells, or sub-cellular regions across a gap between the target substrate and the receiving substrate or collection vessel and onto the receiving substrate or into the collection vessel.

2. The method of claim 1, wherein the energized interlayer remains substantially intact and adhered to the substrate.

3. The method of claim 1, wherein the energized interlayer is removed.

4. The method of claim 1,
   wherein the transfer material comprises a biomatrix; and
   wherein the transfer occurs through evaporation of a portion of the biomatrix adjacent to the energized interlayer.

5. The method of claim 1, wherein the transfer occurs through photomechanical shock.

6. The method of claim 1, wherein the transfer occurs through photothermal shock.

7. The method of claim 1, wherein the transfer occurs through ablation of the interlayer.

8. The method of claim 1, wherein the photon transparent support comprises quartz.

9. The method of claim 1, wherein the photon transparent support comprises a material selected from the group consisting of a glass, a salt, and a polymer.

10. The method of claim 1, wherein the interlayer comprises titanium dioxide.

11. The method of claim 1, wherein the interlayer is about 1 Angstroms to about 10 microns thick.

12. The method of claim 1, wherein the photon energy source is a pulsed laser.

13. The method of claim 12, wherein the laser energy has a fluence between about 1 and about 1000 mJ/cm$^2$.

14. The method of claim 12, wherein the laser energy has a fluence of at least about 0.1 mJ/cm$^2$.

15. The method of claim 12, wherein the laser energy has a fluence of at least about 1 nJ/cm$^2$.

16. The method of claim 1, wherein the photon energy source is a continuous laser.

17. The method of claim 1, wherein the photon energy source is a flash lamp.

18. The method of claim 1, wherein the photon energy source is a maser.

19. The method of claim 1, wherein the target substrate and the photon energy source are moveable with respect to each other.

20. The method of claim 1, wherein the step of providing a target substrate is repeated one or more times using one or more additional target substrates comprising one or more different transfer materials.

21. The method of claim 1, wherein the target substrate comprises a plurality of regions comprising different cells and regions of tissues.

22. The method of claim 1, wherein the biological material comprises histopathologically processed tissue/cells processed according to the steps of:
   providing a thin section of the tissue;
   placing the thin section onto the interlayer;
   dehydrating the thin section with an alcohol; and
   rehydrating the thin section with a buffer containing glycerol.

23. The method of claim 22, wherein the dehydrating step comprises successive washes in alcohol/water solutions having increasing percentages of alcohol.

24. The method of claim 23, further comprising a final wash in about 100% alcohol.

25. The method of claim 22, wherein the thin section contains paraffin.

26. The method of claim 25, further comprising the step of:
deparaffinizing the thin section.

27. The method of claim 22, further comprising the step of:
staining the thin section.

28. The method of claim 27, wherein the staining is performed using a stain selected from the group consisting of but not limited to eosin, hematoxylin, methyl green, and Wright's stain.

29. The method of claim 1, wherein the receiving substrate or collection vessel comprises a microcentrifuge tube.

30. The method of claim 29, further comprising the step of:
performing an assay, biochemical or physical, on the collected cells, groups of cells, or sub-cellular regions.

31. The method of claim 1, wherein the particular cells, groups of cells, or sub-cellular regions comprise a substantially homogenous population of cells.

32. The method of claim 1, wherein the particular cells, groups of cells, or sub-cellular regions comprise cells of a specific and defined population of cells.

33. The method of claim 1, wherein the particular cells, groups of cells, or sub-cellular regions comprise diseased cells.

34. The method of claim 1, wherein the particular cells, groups of cells, or sub-cellular regions are selected by visual identification using a microscope objective, a video camera, and a video screen.

35. The method of claim 1, wherein the histopathologically processed or frozen tissue/cell materials are histopathologically processed or frozen tissue.

36. The method of claim 1, further comprising:
performing the method a plurality of times;
wherein the plurality of transferred particular cells, groups of cells, or sub-cellular regions are collected in the same collection vessel; and
performing a physical assay, biochemical assay, visual assay, biological assay, proteomic assay, genomic assay, or general molecular biology assay on the collected cells, groups of cells, or sub-cellular regions.

37. The method of claim 1, wherein the receiving substrate or collection vessel is a collection vessel.

* * * * *